(12) United States Patent
Biederman et al.

(10) Patent No.: US 7,588,704 B2
(45) Date of Patent: Sep. 15, 2009

(54) ONLINE CONTROL OF BLOWING AGENT CONTENT OF POLYMER BEADS FOR MAKING LOST FOAM PATTERNS

(75) Inventors: Scott W. Biederman, New Boston, NH (US); Timothy S. Rider, Exeter, NH (US)

(73) Assignee: GM Global Technology Operations, Inc., Detroit, MI (US)

( * ) Notice: Subject to any disclaimer, the term of this patent is extended or adjusted under 35 U.S.C. 154(b) by 704 days.

(21) Appl. No.: 11/189,564

(22) Filed: Jul. 26, 2005

(65) Prior Publication Data

US 2007/0023969 A1    Feb. 1, 2007

(51) Int. Cl.
   *B29C 44/34*    (2006.01)
(52) U.S. Cl. .................. 264/51; 264/40.1; 264/40.4; 425/143; 425/4 R; 425/817 R
(58) Field of Classification Search .................. 264/51, 264/40.1, 40.4; 425/143, 4 R, 817 R, 135
   See application file for complete search history.

(56) References Cited

U.S. PATENT DOCUMENTS

| | | | | |
|---|---|---|---|---|
| 4,042,541 A * | 8/1977 | Watts | ............................ | 521/56 |
| 5,385,698 A | 1/1995 | Bishop et al. | .................. | 264/53 |
| 5,479,815 A * | 1/1996 | White et al. | .................. | 73/23.3 |
| 6,521,148 B2 * | 2/2003 | Qiu et al. | .................... | 264/46.4 |
| 6,846,446 B2 * | 1/2005 | Mbachu et al. | ............. | 264/406 |
| 2004/0195714 A1 * | 10/2004 | Mbachu et al. | ............. | 264/40.1 |
| 2006/0144126 A1 * | 7/2006 | O'Brien et al. | ............. | 73/23.42 |
| 2007/0221568 A1 * | 9/2007 | Nagashiki et al. | ...... | 210/500.36 |

OTHER PUBLICATIONS

Chung, H; Lee, H; Jun, C-H; "Determination of Research Octane Number using NIR Spectral Data and Ridge Regression", Bul. Korean Chem. Soc. 2001, vol. 22, No. 1, pp. 37-42.
Boelens, H; Kok, W; DeNoord, O; Smilde, A; "Fast On-Line Analysis of Process alkane Gas Mixtures by NIR Spectroscopy", Applied Spectroscopy, vol. 54, No. 3, 2000, pp. 406-412.
Martens, A; Cermelli, I; Descales, B; Llinas, J; Vidal, J; and Margail, G, "NIR process control of a steam cracker", Cent. Rech., BP Chem. SND, Lavera, Fr. Editor(s): Murray, Ian, Cowe, Ian A. Making Light Work: Adv. Near Infrared Spectrosc., Int. Conf. Near Infrared Spectros. (1992), Meeting Date 1991, 477-481. Publisher: VDH, Weinheim, Germany CODEN: 58QEA9 Conference written in English. CAN 118:127888 AN 1993:127888 CAPLUS (Copyright 2004 ACS on SciFinder R).

* cited by examiner

*Primary Examiner*—Joseph S. Del Sole
*Assistant Examiner*—David N Brown, II
(74) *Attorney, Agent, or Firm*—Fraser Clemens Martin & Miller LLC; J. Douglas Miller

(57) ABSTRACT

The invention involves the real-time, NIR-spectroscopic, closed-loop control of the blowing agent content of polymer beads used to make lost foam casting patterns.

13 Claims, 3 Drawing Sheets

_US 7,588,704 B2_

ONLINE CONTROL OF BLOWING AGENT CONTENT OF POLYMER BEADS FOR MAKING LOST FOAM PATTERNS

TECHNICAL FIELD

This invention relates to making patterns for the lost foam casting process, and more particularly to controlling the blowing agent content of the polymer beads used to make such patterns.

BACKGROUND OF THE INVENTION

The so-called "lost-foam" casting process is a well known technique for producing metal castings wherein a fugitive, pyrolizable, polymeric, foam pattern (including gates, runners, risers, etc.) is covered with a thin (i.e. 0.25-0.5 mm) gas-permeable, ceramic coating, and embedded in an unbonded sand mold to form a mold cavity within the sand. Molten metal (e.g. iron or aluminum inter alia) is then introduced into the mold, from above or below, to pyrolize, and displace the pattern with molten metal. Gaseous and liquid pyrolysis products escape through the gas-permeable, ceramic coating into the interstices between the unbonded sand particles. Typical fugitive polymeric foam patterns comprise expanded polystyrene foam (EPS), polymethylmethacrylate (PMMA), and certain copolymers.

A new pattern is needed for each casting, and must accurately duplicate the dimensions and shape of the casting to be produced. The dimensional accuracy of the castings is no better than the dimensional accuracy of the patterns that produce them. If there are variations between the patterns, or if there are differences between the actual pattern dimensions and the intended pattern dimensions, it will be necessary either to scrap the patterns if they are too small, or to perform extra machining of the castings if they are too large.

While the invention is described hereinafter in terms of patterns made from EPS beads having a pentane (i.e. n-pentane, isopentane and/or cyclopentane), blowing agent, it is to be understood that the invention is likewise applicable to other polymeric foams and blowing agents. To make EPS lost-foam patterns, partially pre-expanded EPS beads are blown into a mold, and therein subjected to steam to complete their expansion and fuse them together into a unitary mass. More specifically, raw so-called T-size (i.e. 0.25 mm diameter, 40 lbs./ft3 density) EPS beads are formed from polystyrene containing about 6.0 percent by weight of a pentane blowing agent. The raw beads are too dense, and contain too much blowing agent, for "as is" use in a one-step pattern-molding operation. Accordingly before molding the patterns, it is common practice to subject the beads to a pre-expansion operation wherein they are heated, and partially expanded to reduce their density to about 1.4 lbs/ft$^3$, and their pentane content to about 4%-5%. Pre-expansion equipment is commercially available for this purpose. In one pre-expansion technique, the raw beads are charged into a closed vessel having an expansion chamber where they are contacted with saturated steam at low super atmospheric pressure, which gasifies the pentane, expands the beads diametrically fourfold (i.e. to about 1 mm), and drives off some of the pentane. Thereafter, the beads are cooled by standing, or by fluidization in ambient air. The pre-expanded beads have a cellular structure, and are close to the bead size used to mold the patterns. In another pre-expansion technique, the beads are not directly exposed to the steam, but rather are heated at about 200° F. in the expansion chamber through contact with a steam jacket, to expand and partially degas (i.e. remove pentane) them, and then water-cooled to arrest their expansion. The pre-expanded beads are then screened to remove any unexpanded raw beads and/or any clumps of beads that might have formed.

The mold used to make the pattern from the pre-expanded beads has perforate walls defining a mold cavity through which 240° F. steam enters the mold cavity. In the "flow-through" steaming technique, steam is introduced, through one of the mold segments on one side of the mold cavity, passes through the beads in the mold cavity, and exits the mold cavity through the other mold segment on the opposite side of the mold cavity. An alternative steaming technique is known as "autoclaving" which involves pressurizing both segments at the same time so as to soak the beads in the steam for a sufficient duration to expand and fuse them together. Following steaming, the pattern is cooled to about 140° F. by spraying water onto the backside of the mold segments, and/or by the application of vacuum to the steam chests until the expansion of the beads is arrested.

In an attempt to provide reproducible, dimensional stability from one pattern to the next, and thus from one casting to the next, it was an early practice to age the pre-expanded beads before molding to obtain a prescribed pentane content in the beads, and to age the patterns after molding so that they all come to a reproducible final configuration/dimension. In one practice, the pre-expanded beads were stored for 24 hours before pattern molding, and the patterns were stored from 6-72 hours before use to allow their pentane content to stabilize, and any water therein to evaporate. Shorter aging times (e.g. 2-6 hours) were made possible by force-aging the patterns in a circulating-air oven at a temperature of about 165° F.

To avoid significant variations in the pentane content of the pre-expanded beads being supplied to the pattern-molding machine, Bishop U.S. Pat. No. 5,385,698 (which is assigned to the Assignee of this invention, and is hereby incorporated by reference) proposed a technique for making dimensionally accurate lost foam patterns without the need for extended aging of either the pre-expanded beads or the finished patterns. Bishop seeks to control the pentane content of the pre-expanded beads supplied to the pattern-molding machines within defined limits, by conditioning them for about 60 to 90 minutes in a so-called "pentane reduction chamber" (hereafter PRC)". In the PRC, a stream of hot (preferably ca. 170° F.) air fluidizes the beads, and strips away any excess pentane therefrom so as to provide pre-expanded beads that have a pentane content less than 3.75%. While the invention is described herein in the context of "air" as being the fluidizing gas in the PRC, it is to be understood that other gases, such as nitrogen, helium, argon, $CO_2$, etc., that are unreactive with styrene or pentane, and that do not interfere with the quantitative, spectroscopic analysis of pentane in the presence of polystyrene, may be substituted for some, or all, of the air.

It has been shown that the degree of pattern fusion influences the way the metal fills the casting cavity in the sand. Poor fusion, resulting from too low pentane content, results in turbulent metal fronts that move erratically through the foam pattern causing porosity and poor casting quality. Good fusion, resulting from higher pentane content, causes a more controlled metal front and fewer casting defects. By controlling the amount of pentane in the beads to provide consistent levels of pentane in the beads supplied to the pattern mold, more consistent levels of fusion are obtained, and consequently more consistent casting quality.

Bishop attempts to control the pentane content of the pre-expanded beads by fixing the duration of the hot-air-fluidization step undertaken in the PRC. The duration chosen is based on day-to-day practical experience operating the PRC, and empirical, off-line (i.e. tests conducted remote from the bead handling/conditioning equipment) thermo-gravimetric tests wherein samples of the beads are weighed, heated to drive off the pentane, and weighed again to determine their weight loss. Alternative, off-line, analytical tests such as gas chromatography or NIR-spectroscopy have been proposed by others.

Tighter control of the pentane content of the pre-expanded beads than is possible with the Bishop technique is needed to keep the pentane content within a preferred prescribed narrow range of about 1.4% to 2.5% by weight. The present invention is directed toward making patterns for the Lost Foam process that are dimensionally stable/consistent by the periodic, real-time, online (i.e. pentane analyzer is coupled directly with the bead handling/conditioning equipment for closed-loop control of pentane content), measurement of the pentane content in the pre-expanded beads used to make the pattern, and in response thereto, automatically either (a) adjusting the operating conditions of the PRC to keep the pentane content within the prescribed range, (b) adjusting the pattern-molding conditions to accommodate beads whose pentane-content is outside the prescribed range, or (c) shutting down the pattern-mold(s) when the pentane content of the beads enroute to the pattern mold falls outside the prescribed range. Real-time (i.e. within about 15 secs.) on-line, measurements of the pentane content of the beads may be taken in situ at various sites throughout the bead handling/conditioning apparatus/equipment (e.g. in the PRC, storage vessels or bead transfer ducts/lines), using a near-infrared (NIR) spectroscopic sensor coupled with the equipment at such sites.

BRIEF DESCRIPTION OF THE INVENTION

Process-wise, the invention involves a method of making lost foam casting patterns from polymer beads having a first density and first blowing agent content too high for molding the patterns directly therefrom. The method involves: (a) first heating and pre-expanding the beads to a second density and a second blowing agent content lower than the first density, and first blowing agent content, respectively, but still to too high for molding into dimensionally stable patterns; (b) second heating the pre-expanded beads in an upward flowing stream of hot air, inter alia, at a temperature, and for a time, sufficient to reduce the blowing agent content of the pre-expanded beads to within a prescribed range suitable for molding the beads into dimensionally stable patterns; (c) charging a pattern-mold with beads having the prescribed blowing agent content; and (d) heating the beads in the pattern-mold to expand, shape and bond them together into a Lost Foam casting pattern: The invention contemplates improving the aforesaid method by controlling the operation of the process by providing on-line, real-time, NIR-spectroscopic measurement of the blowing agent content of the beads at various stages of the process, and in response thereto, either maintaining the status quo of the operating conditions of the process, or automatically initiating adjustment of the operating conditions of the process either (1) to produce beads within the prescribed range, (2) shut down the pattern-molding operation until such beads can be produced, or (3) to mold acceptable patterns from beads whose blowing agent content is outside the prescribed range. In one embodiment, the NIR-spectroscopic measuring takes place during, and at the site of, the second heating (i.e. in the PRC) to allow for adjustment of the PRC's operating conditions to bring the beads into spec. (i.e. within the prescribed blowing agent content). In another embodiment, the NIR-spectroscopic measuring takes place at the entrance to the pattern-mold to allow for last minute changing of the pattern molding conditions to accommodate beads whose blowing agent content is outside the prescribed range, or for shutting down of the pattern mold until the proper blowing agent content can be restored to the beads. Preferably, the blowing agent is pentane, the second heating utilizes 150° F. to 200° F. hot air, and the prescribed range is between about 1.4% to about 2.5% by weight pentane.

Equipment-wise, the invention contemplates apparatus for making lost foam casting patterns from polymer beads having a first density and a first blowing agent content. The apparatus includes: a pre-expansion vessel for first heating the beads and gasifying the blowing agent to expand the beads into a mass of pre-expanded beads having a second density and second blowing agent content less than the first density and first blowing agent content; a blowing agent reduction chamber for second heating the pre-expanded beads for a long enough time to reduce the blowing agent content thereof to within a prescribed range of blowing agent contents suitable for molding the beads into dimensionally stable casting patterns; a blower supplying a stream of gas to the chamber for fluidizing and second heating the pre-expanded beads in the chamber; a heater heating the gas supplied to the chamber; a storage vessel for receiving and storing the pre-expanded beads from the blowing-agent reduction vessel; a pattern-mold that receives beads from the storage vessel for molding into a casting pattern; a NIR-sensor coupled to the apparatus for directing a NIR-beam onto the beads in the apparatus to spectroscopically measure the blowing agent content of the beads; and a controller associated with, and responsive to, the NIR-sensor to automatically initiate such adjustments to the operation of the apparatus as may be needed either to produce beads having a blowing agent content within the prescribed range, to mold acceptable patterns from beads whose blowing agent content is outside the prescribed range, or shut down the pattern-mold if the blowing agent content of the beads about to enter the pattern-mold is outside the prescribed range.

BRIEF DESCRIPTION OF THE DRAWINGS

The invention will be better understood when considered in the light of the following detailed description thereof which is given hereafter in conjunction with the following drawings of which.

DETAILED DESCRIPTION OF SPECIFIC EMBODIMENT

Figure 1:
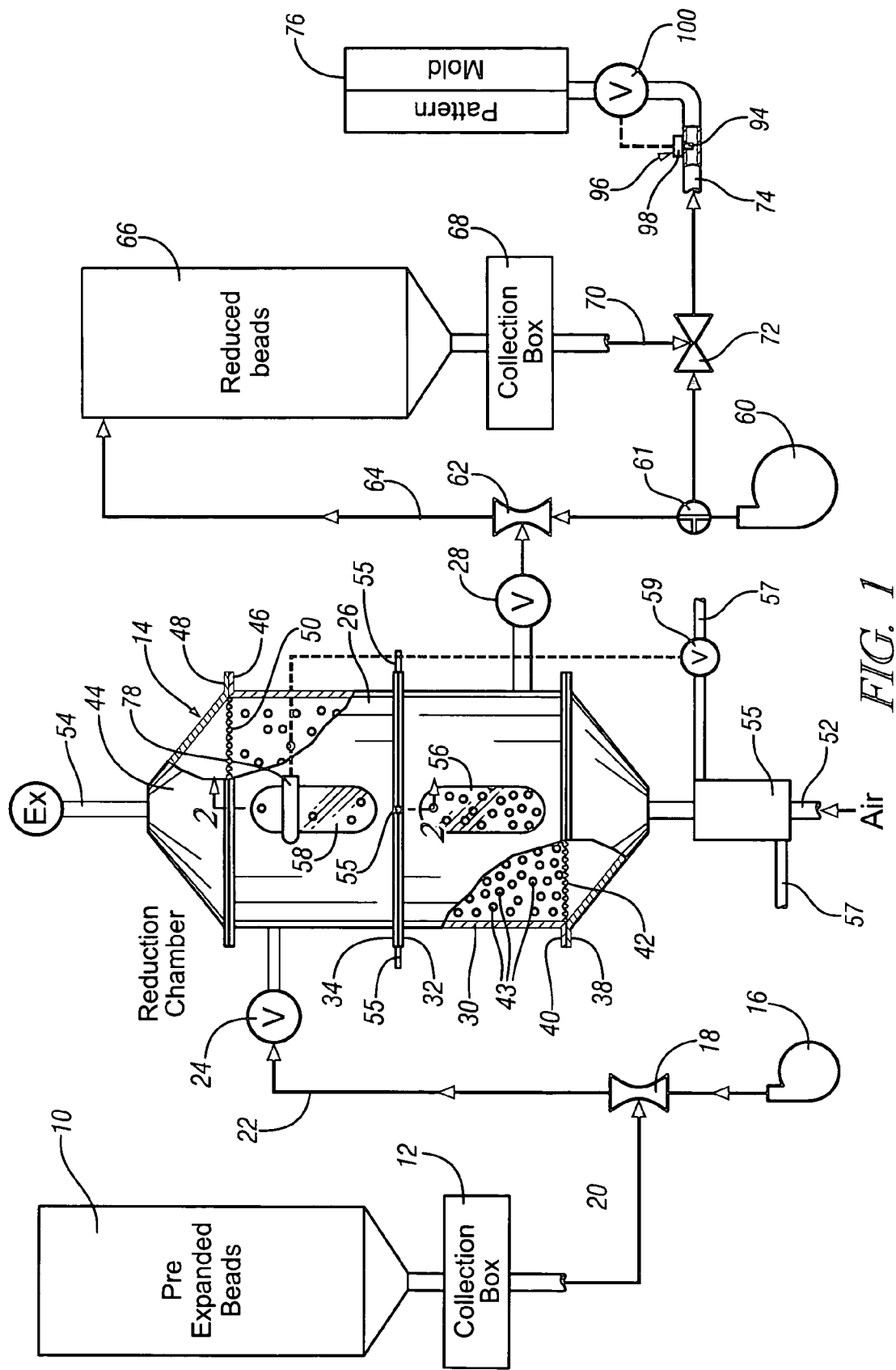
FIG. 1 illustrates a pentane reduction system in accordance with the present invention.

FIG. 1 illustrates a pentane reduction system in accordance with the present invention. Pre-expanded beads are transferred (e.g. blown) from a pre-expansion apparatus (not shown) into a permeable storage vessel 10 where they reside until needed. When needed, the beads flow by gravity into a collection box 12, and are thence blown into a Bishop-type pentane reduction chamber 14. Transport of the pre-expanded beads from vessel 10 into the pentane reduction chamber 14 is preferably effected by a blower 16 that blows a stream of ambient air through a jet pump or ejector 18 that comprises a venturi nozzle. As the air passes through the venturi nozzle, it develops suction that draws air and pre-expanded beads through line 20 and entrains them in the air-stream flowing through line 22 past then-open valve 24 into the top of the cylindrical pentane reduction chamber 14. As soon as a predetermined quantity of pre-expanded beads has been transferred into the pentane reduction chamber 14, valve 24 is closed. Valve 28 near the bottom of chamber 14 is also closed at this stage of the operation. The pentane reduction chamber 14 is a cylinder comprising upper cylindrical section 26 and lower cylindrical section 30, which are bolted together at flanges 32 and 34. The lower section 30 of vessel 14 is closed with a generally conical section 36, which is bolted to the lower cylindrical portion 30 at flanges 38 and 40. Secured between flanges 38 and 40 is a screen 42 at the lower end of the vessel for supporting the beads 43 in the chamber 14 when they are at rest. At the upper end of the pentane reduction chamber 14 is an upper conical section 44 that is attached to the upper cylindrical section 26 at flanges 46 and 48. Secured between flanges 46 and 48 is upper screen 50 which serves to retain the beads in the vessel when they are treated in a hot air stream as will be described below. Chamber 14 is adapted to receive a stream of hot air through duct 52 at the lower end, and to exhaust the air at the top through an exhaust duct 54. A blower (not shown) supplies air to the duct 52. A heater heats the air entering the duct 52. For example, a heat exchanger 55 transfers heat from a heating fluid that flows in line 57 to the air 52. Sight-glasses 56 and 58 enable the beads in the pentane reduction chamber to be observed, and spectroscopically analyzed as will be discussed hereinafter.

Operation of the PRC is illustrated by the following specific example. 175-200 pounds of pre-expanded polystyrene beads having a density of 1.30-1.45 lbs/ft$^3$ and a pentane content of 4.5% by weight, are conditioned in a PRC 14 that is 6 feet in diameter and 15 feet tall. A stream of 170° F. air is flowed upwardly through the PRC at a flow rate of 2100 ft$^3$/min for about 60-90 minutes, as determined by the on-line pentane sensor 78, to reduce the pentane content to less than about 2.5%. A relatively small amount of ambient air may be blown through tubes 55 into the suspended beads to further stir and mix them for more effective treatment by the hot air stream. When the $\leq$2.5% pentane level is reached, the hot air flow is stopped and the beads allowed to settle onto the bottom screen 42 for cooling. Alternatively, the upward air flow could be allowed to continue, but the flow of heating fluid in line 57 stopped by valve 59, so that ambient temperature air cools the pre-expanded beads suspended therein before the fluidizing air is stopped and the beads allowed to settle onto the screen 42.

The beads are then removed from the chamber 14 to a permeable holding vessel 66 by opening valve 28 and energizing blower 60 which forces a stream of ambient air through ejector 62 to draw pentane-reduced beads through valve 28 and conduct them through line 64 into the top of a permeable vessel 66 where they are allowed to further cool and to equalize and stabilize their pentane content. When beads are needed for pattern molding, they are dropped into collection box 68 and thence transported through duct 70, injector 72 and duct 74 to the pattern-molding machine 76. A two-way valve 61 allows the blower 60 to supply air to either the ejector 62 when filling the vessel 66, or to ejector 72 when transferring beads from the storage vessel 66 to the pattern-mold 76 via duct 74. In the position shown, the valve 61 would direct air to the ejector 62 for transferring the beads into the storage vessel 66. Counterclockwise rotation of the valve 61 ninety degrees would direct air to the injector 72 for transfer of the beads to the pattern-mold 76. Alternatively, the beads are first transferred to a permeable holding vessel, and thence gravity fed into a manually portable bead storage cart for moving the beads to the pattern mold. The beads are sucked out of the cart and into the pattern mold. A NIR-spectroscopic pentane sensor-measures the pentane content of the beads as they are being sucked out of the cart at the entrance to the pattern-mold, and initiates appropriate corrective action (e.g. mold shut down) when the pentane content of the beads is outside the prescribed range.

Figure 2:
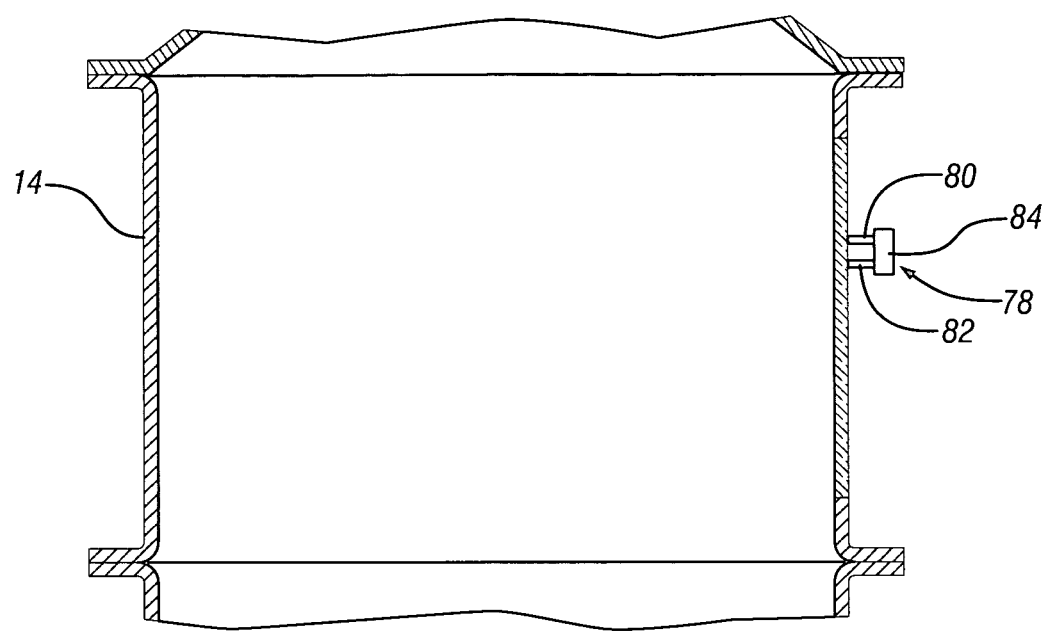
FIG. 2 is a section view taken in the direction 2-2 of FIG. 1.
Figure 3:
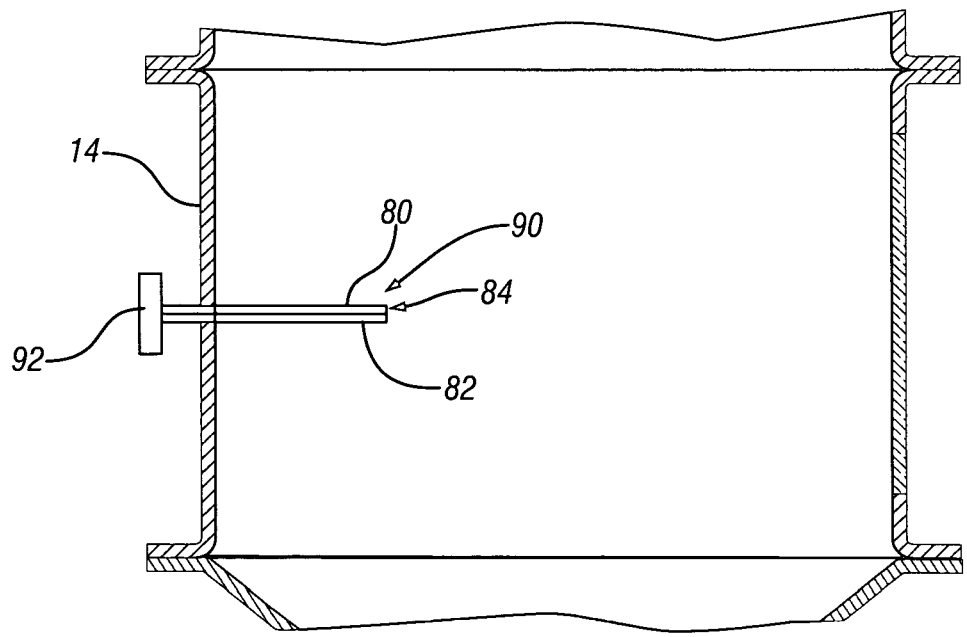
FIG. 3 is a view similar to that of FIG. 2 except for a different embodiment.

According to one embodiment of the present invention (see FIG. 2), a near infra-red (NIR) spectroscopic sensor 78 (e.g. Bruker Optics' Model Q410/A) is positioned adjacent the sight-glass 58, and includes a NIR-emitter 80 for projecting a NIR beam through the glass onto the pre-expanded beads in the chamber 14, a NIR-detector 82 for receiving such of the projected NIR beam as is not absorbed, and is reflected, by the pre-expanded beads in the PRC 14 (hereafter the residual NIR beam), and a controller 84 for analyzing the character of the residual NIR-beam to determine the pentane content of the beads, and, based thereon, automatically initiating adjustments to the PRC's operating conditions (e.g. bead residence time in the chamber, air temperature, air flow rate, etc.), as may be needed, to bring the pentane content of the beads exiting the PRC to within prescribed limits. In this embodiment, both the emitter 80 and collector 83 are located outside the chamber 14. In a preferred embodiment of the invention (see FIG. 3), a probe 90 (e.g. Bruker Optics' Model IN261-3), comprising an elongated, narrow bundle of many fiber optic NIR-emitters 86 and NIR-receivers 88, is inserted through a port in the wall of the chamber 14, and into the bed of fluidized beads. A controller 92 analyzes the character of the residual beam, determines the pentane content of the beads, and initiates whatever, if any, system adjustments may be needed to bring the pentane content of the beads exiting the PRC to within prescribed limits. In each embodiment, it may be desirable to reduce the flow rate (e.g. to about 100 scfm) of fluidizing hot air passing through the PRC while the beads are being analyzed by the spectroscopic sensor to expose a higher concentration of beads to the emitted NIR beam than if the higher flow rate were used.

According to still another embodiment of the invention, a combined emitter/detector elongated fiber optic probe 94, of a NIR-spectroscopic sensor 96, is inserted in the supply line 74 at the entrance to the pattern-mold 76 to measure the pentane content of the beads being supplied to the pattern-mold. If the pentane content is not within the limits prescribed for the beads at this stage in the process, the controller 98 initiates adjustments to the pattern molding conditions to accommodate the out-of-range beads, or shut down the pattern-mold (e.g. by closing inlet valve 100).

To make the real-time NIR-spectroscopic determination of the pentane-content of the beads, a spectroscopic sensor projects a NIR beam onto a sample of the beads under scrutiny. The beads absorb certain wavelengths of the projected beam, and reflect the remaining, unabsorbed wavelengths of the projected beam (i.e. residual NIR beam) into the sensor's detector. A spectrum is generated that shows which frequencies, and the amount thereof (i.e. as a percent of the projected NIR-beam), that have been absorbed by the beads. Each pentane concentration will have its own unique spectrum, e.g. see FIG. 4 which shows spectra for raw beads containing 6.18% pentane (solid line), and pre-expanded beads containing 1.44% pentane (dashed line). Using suitable commercially available pattern recognition software, the spectroscopic sensor's controller compares the spectrum from the beads under scrutiny to a library of reference spectra previously empirically correlated to beads having known pentane contents (hereafter signature spectra). When a match, or near match, is found between the spectrum of a bead sample under scrutiny and a signature spectrum, the pentane content of the sample is revealed. If the pentane content of the sample falls within a prescribed range of acceptability, no corrective action will be taken (i.e. the status quo of the system will be maintained). If on the other hand, the pentane content of the sample falls outside the prescribed range, the controller will either initiate appropriate corrections to the system's operating conditions to bring the pentane back into the prescribed range, or to modify the pattern molding conditions to accommodate the out-of-range beads or to shut down the pattern mold(s) until the situation is corrected. Hence for example, a spectroscopic sensor monitoring the pentane content of the beads in the PRC might initiate (1) varying the residence time of the beads in the PRC, or (2) varying the temperature and/or flow rate of the hot fluidizing air to insure a pentane content within the prescribed limits. In another example, the spectroscopic sensor may be located at the entrance to the pattern-mold to monitor the pentane content of the beads just before they enter the pattern-mold, and to initiate adjustment to, or shut down of, of the pattern-mold operation. Finally, the NIR-spectroscopic sensor may be used to measure the pentane content of a finished pattern, and adjust the aging time thereof as may be needed.

Figure 4:
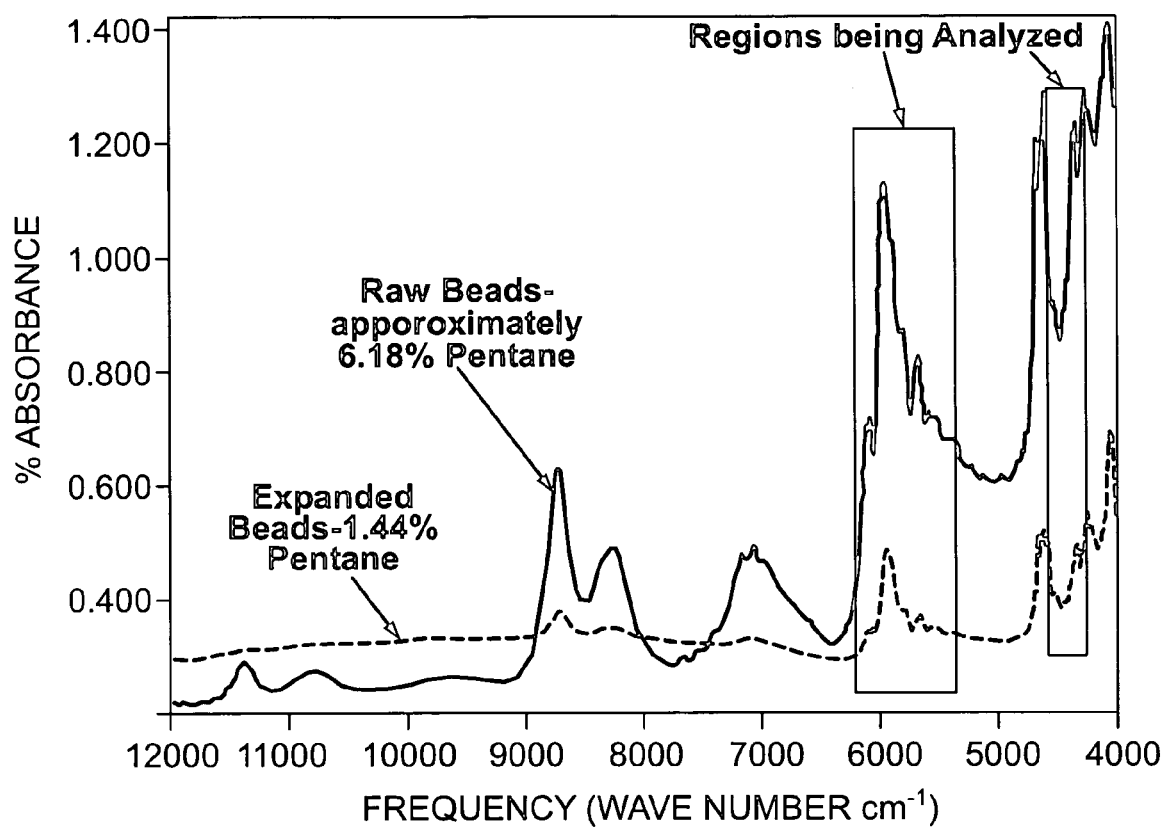
FIG. 4 shows spectra for two beads having different pentane contents.

To build the library of reference/signature spectra used in our work, over 100 bead samples, having different pentane contents, were analyzed, in the laboratory, using both (1) a model 5890 Series II gas chromatograph from Hewlett Packard, and (2) a model Matrix-I NIR-spectrometer from Bruker Optics. The % pentane measured with the gas chromatograph was assumed to be the "true" value. The results of both the GC and NIR analyses were correlated with each other such that specific spectra were identified as corresponding to specific known pentane contents. More specifically, the beads under scrutiny were either placed in a glass vial, or in a rotating sample cup, and NIR-beam from a laboratory spectrometer projected onto the beads. Reflected light from the beads was directed to the NIR-detector of the spectrometer, and an interferogram generated. A Fourier transform was applied to generate a sample singlebeam spectrum, which was ratioed to a reference singlebeam that was the same as the projected beam, and a transmission spectrum generated. The log of the transmission spectra was then taken to generate an absorbance spectrum which was linear with concentration, and where bands in the spectrum relate to the light that is absorbed by the sample (i.e. the higher the concentration the larger the band). FIG. 4 shows two spectra representing beads having different pentane concentrations. The multivariate data collected was inputted to Bruker Optics' OPUS chemometrics software which was embedded in the spectrometer's controller, and a model generated that represented the best correlation between the gas chromatographic measurements and the spectra collected by the NIR-spectrometer. That work identified the frequencies (as wave numbers) between 5446-6102 $cm^{-1}$ and 4602-4247 $cm^{-1}$ as being the best regions for quantifying the pentane content in polystyrene beads. Other gas chromatographs, NIR-spectrometers and chemometrics software are expected to yield similar results.

The controllers 84, 92 include a common digital computer with associated: read-only memory (ROM); read-write random access memory (RAM); electrically programmable read-only memory (EPROM); memory for storing a library of empirically predetermined reference spectra signatures for comparing to spectra from beads under scrutiny; and input/output sections which interface with the devices (i.e. process equipment) needed to control the operating conditions of the PRC and pattern-mold, or to shut down the pattern-mold, as needed. The read-only memory (ROM) contains the instructions necessary to implement the basic input/output instructions. The electrically programmable read-only memory (EPROM) contains the instructions necessary to implement the data processor's own internal control, data manipulation, and communication algorithms. The controllers 84, 92 communicate with the PRC and pattern-mold control devices by means of any appropriate communication network protocol, many of which are known in the art. A standard Pentium computer running Windows 2000, XP or better is adequate for this purpose. A specific program for carrying out the functions of the controller may be accomplished by standard skill in the art using conventional information processing languages.

The controller is programmed to perform the process of the present invention. That is to say, the spectra data from the beads being scrutinized are fed to the controller. These spectra are then compared to the reference spectra signatures stored in controller's memory. If the controller finds a match between a spectrum from beads being scrutinized and a reference spectra signature, and the pentane-content corresponding thereto is outside the prescribed range, it issues a control signal to the appropriate process equipment (e.g. valves, timers, air pumps, etc.) to take whatever corrective action is needed to bring the pentane content into the prescribed range. The controller repeats the process according to a predetermined schedule, which may have longer intervals at the beginning (e.g. every 15 minutes) of the pentane-reduction process, and shorter intervals (e.g. every 1-2 minutes) near the end of the process.

While the invention has been described in terms of a specific embodiment thereof it is not intended to be limited thereto, but rather only to the extent set forth hereafter in the claims that follow.

The invention claimed is:

1. In a method of making lost foam casting patterns from polymer beads having a first density and a first blowing agent content comprising:
   (a) first heating said beads to pre-expand them into a batch of pre-expanded beads having a second density lower than said first density, and a second blowing agent content less than said first blowing agent content, but to too high for molding into dimensionally stable patterns;
   (b) second heating the pre-expanded beads in a stream of a hot gas for a time sufficient to reduce the blowing agent content of the pre-expanded beads to within a prescribed range of blowing agent contents suitable for molding the beads into dimensionally stable patterns, said gas being selected from the group consisting of gases that are unreactive with said polymer and said blowing agent, and do not interfere with the quantitative spectroscopic analysis of said blowing agent in the presence of said polymer beads;
   (c) charging a pattern-mold with beads having a blowing agent content within said prescribed range; and
   (d) heating the beads in said pattern-mold to further expand, shape and bond them together to form a casting pattern, the improvement comprising controlling the operation of said method by the regular, on-line, real-time NIR-spectroscopic measurement of the blowing agent content of the beads, and in response thereto automatically initiating such adjustments to the operating conditions of said second heating as may be needed to produce beads within said prescribed range.

2. The method as recited in claim 1 wherein: said polymer beads comprise polystyrene; said blowing agent comprises pentane; and said hot gas stream comprises air that has a temperature of about 150°F.-200°F., and that continues to flow until said measuring determines that said prescribed range has been attained and initiates termination of said second heating.

3. The method according to claim 1 wherein said measuring is accomplished during, and at the site of, said second heating.

4. The method according to claim 1 wherein said measuring is accomplished at the entrance to said pattern-mold.

5. The method according to claim 2 wherein said prescribed range comprises about 1.4% to 2.5% by weight pentane.

6. In apparatus for making lost foam casting patterns from polymer beads having a first density and a first blowing agent content including,
(i) a pre-expansion vessel adapted to first heat said beads and gasify said blowing agent to expand said beads into a mass of pre-expanded beads having a second density and second blowing agent content less than said first density and first blowing agent content,
(ii) a blowing agent reduction chamber adapted to second heat said pre-expanded beads for a time sufficient to reduce the blowing agent content of said pre-expanded beads to within a prescribed range of blowing agent contents suitable for molding the beads into dimensionally stable casting patterns,
(iii) a blower supplying a stream of gas to said chamber to fluidize and second heat said pre-expanded beads in said chamber,
(iv) a heater heating said hot gas supplied to said chamber,
(v) a storage vessel receiving said pre-expanded beads from said blowing agent reduction vessel, and
(vi) a pattern-mold receiving beads from said storage vessel for molding into said pattern, the improvement comprising:
(1) a NIR-sensor coupled to said apparatus and directing a NIR-beam onto the beads in said apparatus to spectroscopically measure the blowing agent content of the beads-, and
(2) a controller associated with, and responsive to, said NIR-sensor to automatically initiate adjustments to the operation of said apparatus as may be needed to produce beads having a blowing agent content within said prescribed range.

7. Apparatus according to claim 6 wherein said NIR-sensor is coupled to, and measures the blowing agent content of the beads in, the blowing-agent reduction chamber, and initiates adjustment to the length of time the beads are heated in said chamber.

8. Apparatus according to claim 7 wherein said blowing agent reduction chamber is defined by a wall that includes a glass window, and said NIR-sensor is coupled to, and directs said NIR-beam through, said window.

9. Apparatus according to claim 7 wherein said blowing agent reduction chamber is defined by a wall that includes a port, and said NIR-sensor includes an elongated probe inserted into said chamber through said port and directing said NIR-beam through, said window.

10. In apparatus for making lost foam casting patterns from polymer beads having a first density and a first blowing agent content including,
(i) a pre-expansion vessel adapted to first heat said beads and gasify said blowing agent to expand said beads into a mass of pre-expanded beads having a second density and second blowing agent content less than said first density and first blowing agent content,
(ii) a blowing agent reduction chamber adapted to second heat said pre-expanded beads for a time sufficient to reduce the blowing agent content of said pre-expanded beads to within a prescribed range of blowing agent contents suitable for molding the beads into dimensionally stable casting patterns,
(iii) a blower supplying a stream of gas to said chamber to fluidize and second heat said pre-expanded beads in said chamber,
(iv) a heater heating said hot gas supplied to said chamber,
(v) a storage vessel receiving said pre-expanded beads from said blowing agent reduction vessel, and
(vi) a pattern-mold having an entrance receiving beads from said storage vessel for molding into said pattern, the improvement comprising:
(1) a NIR-sensor coupled to said apparatus at said entrance to said pattern-mold and directing a NIR-beam into the beads at said entrance to thereat spectroscopically measure the blowing agent content of the beads, and
(2) a controller associated with, and responsive to, said NIR-sensor to automatically initiate adjustments to the operation of said pattern-mold to accommodate pre-expanded beads having a blowing agent content outside said prescribed range.

11. In apparatus for making lost foam casting patterns from polymer beads having a first density and a first blowing agent content including,
(i) a pre-expansion vessel adapted to first heat said beads and gasify said blowing agent to expand said beads into a mass of pre-expanded beads having a second density and second blowing agent content less than said first density and first blowing agent content,
(ii) a blowing agent reduction chamber adapted to receive and second heat said pre-expanded beads for a time sufficient to reduce the blowing agent content of said pre-expanded beads to within a prescribed range of blowing agent contents suitable for molding the beads into dimensionally stable casting patterns,
(iii) a blower supplying gas to said chamber to fluidize and second heat said pre-expanded beads in said chamber,
(iv) a heater heating said hot gas supplied to said chamber,
(v) a storage vessel receiving said pre-expanded beads from said blowing agent reduction vessel, and
(vi) a pattern-mold having an entrance receiving beads from said storage vessel for molding into said pattern, the improvement comprising:
(1) a NIR-sensor coupled to said apparatus at said entrance to said pattern-mold and directing a NIR-beam onto the beads at said entrance to thereat spectroscopically measure the blowing agent content of the beads, and
(2) a controller associated with, and responsive to, said NIR-sensor to automatically initiate shut down of said pattern-mold when said pre-expanded beads at said entrance have a blowing agent content outside said prescribed range.

12. In a method of making lost foam casting patterns from polymer beads having a first density and a first blowing agent content comprising:
(a) first heating said beads to pre-expand them into a batch of pre-expanded beads having a second density lower than said first density, and a second blowing agent content less than said first blowing agent content, but to too high for molding into dimensionally stable patterns;
(b) second heating the pre-expanded beads in a stream of a hot gas for a time sufficient to reduce the blowing agent content of the pre-expanded beads to within a prescribed range of blowing agent contents suitable for molding the beads into dimensionally stable patterns, said gas being selected from the group consisting of gases that are unreactive with said polymer and said blowing agent, and do not interfere with the quantitative spectroscopic analysis of said blowing agent in the presence of said polymer beads;

(c) charging a pattern-mold with beads having a blowing agent content within said prescribed range; and (d) heating the beads in said pattern-mold to further expand, shape and bond them together to form a casting pattern, the improvement comprising controlling the operation of said method by the on-line, real-time NIR-spectroscopic measurement of the blowing agent content of the beads, and in response thereto automatically initiating such adjustments to the operating conditions of said pattern-mold as may be needed for said pattern-mold to mold acceptable patterns from beads whose blowing agent content is outside said prescribed range.

13. In a method of making lost foam casting patterns from polymer beads having a first density and a first blowing agent content comprising:

(a) first heating said beads to pre-expand them into a batch of pre-expanded beads having a second density lower than said first density, and a second blowing agent content less than said first blowing agent content, but to too high for molding into dimensionally stable patterns;

(b) second heating the pre-expanded beads in a stream of a hot gas for a time sufficient to reduce the blowing agent content of the pre-expanded beads to within a prescribed range of blowing agent contents suitable for molding the beads into dimensionally stable patterns, said gas being selected from the group consisting of gases that are unreactive with said polymer and said blowing agent, and do not interfere with the quantitative spectroscopic analysis of said blowing agent in the presence of said polymer beads;

(c) charging a pattern-mold with beads having a blowing agent content within said prescribed range; and (d) heating the beads in said pattern-mold to further expand, shape and bond them together to form a casting pattern, the improvement comprising controlling the operation of said method by the on-line, real-time NIR-spectroscopic measurement of the blowing agent content of the beads at the entrance to the pattern-mold, and in response thereto, automatically shutting down said pattern-mold when the beads at said entrance have a blowing agent content that is outside said prescribed range.

* * * * *